United States Patent
Hamel et al.

(10) Patent No.: US 11,944,361 B2
(45) Date of Patent: Apr. 2, 2024

(54) BONE PLATE WITH STRUCTURES FOR ATTACHMENT OF SUTURES

(71) Applicant: DEPUY SYNTHES PRODUCTS, INC., Raynham, MA (US)

(72) Inventors: Ross Hamel, West Chester, PA (US); Glen Pierson, Glenmoore, PA (US); Peter Van Citters, Phoenixville, PA (US); George Mikhail, West Chester, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 436 days.

(21) Appl. No.: 16/536,781

(22) Filed: Aug. 9, 2019

(65) Prior Publication Data

US 2021/0038271 A1 Feb. 11, 2021

(51) Int. Cl.
  *A61B 17/80* (2006.01)
  *A61B 17/04* (2006.01)
  *A61F 2/08* (2006.01)

(52) U.S. Cl.
  CPC ...... *A61B 17/8061* (2013.01); *A61B 17/8004* (2013.01); *A61B 17/8057* (2013.01); *A61B 17/0401* (2013.01); *A61F 2/0811* (2013.01)

(58) Field of Classification Search
  CPC ............ A61B 17/8061; A61B 17/8004; A61B 17/8057; A61B 17/0401; A61F 2/0811
  See application file for complete search history.

(56) References Cited

U.S. PATENT DOCUMENTS

| 6,960,213 B2 | 11/2005 | Chervitz et al. |
| 7,604,657 B2 | 10/2009 | Orbay et al. |
| 7,744,638 B2 | 6/2010 | Orbay et al. |
| (Continued) | | |

FOREIGN PATENT DOCUMENTS

| WO | 20090128846 A1 | 10/2009 |
| WO | 2017/035302 A1 | 3/2017 |
| WO | 2017/120327 A2 | 7/2017 |

OTHER PUBLICATIONS

Written Opinion of International Searching Authority International re Application No. PCT/IB2020i056839; dated Jan. 2015; 8 pgs.
(Continued)

*Primary Examiner* — Jerrah Edwards
*Assistant Examiner* — Christine L Nelson
(74) *Attorney, Agent, or Firm* — Kramer & Amado, P.C.

(57) ABSTRACT

A bone plate system is designed for use on a bone, which may be a humerus. The system includes an elongated bone plate extending along a longitudinal axis, the bone plate having an upper surface, an opposed bone-facing surface, and a boundary edge of the bone plate; and at least one threaded fastener hole extending from the upper surface to the bone-facing surface. The fastener holes are designed to receive a bone fastener to couple the bone plate to the bone. A plurality of first suture-receiving structures are connected with the bone plate and project from the boundary edge of the bone plate, so that the first suture-receiving structures are spaced from each another along the boundary edge of the bone plate. Each of the first suture-receiving structures comprises a wire loop anchored to the upper surface or to the bone-facing surface of the bone plate.

20 Claims, 8 Drawing Sheets

(56) References Cited

U.S. PATENT DOCUMENTS

| | | |
|---|---|---|
| 8,267,973 B2 | 9/2012 | Humphrey |
| 8,469,999 B2 * | 6/2013 | Gonzalez-Hernandez .................. A61F 2/0811 606/232 |
| 8,535,313 B1 | 9/2013 | Masson |
| 8,545,539 B2 | 10/2013 | Spencer |
| 8,728,082 B2 | 5/2014 | Fritzinger et al. |
| 8,790,378 B2 | 7/2014 | Castaneda et al. |
| 8,814,918 B2 | 8/2014 | Orbay et al. |
| 8,821,551 B2 | 9/2014 | Zeetser et al. |
| 8,926,675 B2 | 1/2015 | Leung et al. |
| 8,968,371 B2 | 3/2015 | Humphrey et al. |
| 9,066,805 B2 | 6/2015 | Berchoux |
| 9,113,973 B2 | 8/2015 | Spencer |
| 9,211,151 B2 | 12/2015 | Weaver et al. |
| 9,232,946 B2 | 1/2016 | Fritziner et al. |
| 9,259,217 B2 | 2/2016 | Fritzinger et al. |
| 9,381,053 B2 | 7/2016 | Parsons et al. |
| 9,433,407 B2 | 9/2016 | Fritzinger et al. |
| 9,486,261 B2 | 11/2016 | Plecko et al. |
| 9,504,503 B2 | 11/2016 | Cavallazzi et al. |
| 9,510,881 B2 | 12/2016 | Castaneda et al. |
| 9,549,768 B2 | 1/2017 | Finley |
| 9,730,686 B2 | 8/2017 | Ampuero et al. |
| 9,750,550 B2 | 9/2017 | Leung et al. |
| 9,801,625 B2 | 10/2017 | Dooney, Jr. et al. |
| 9,833,230 B2 | 12/2017 | Stone |
| 9,855,083 B2 | 1/2018 | Mighell et al. |
| 9,877,757 B2 | 1/2018 | Berchoux et al. |
| 9,907,586 B2 | 3/2018 | Levy et al. |
| 10,010,423 B2 | 7/2018 | Kumar |
| 10,182,853 B2 | 1/2019 | Conley et al. |
| 10,231,762 B2 | 3/2019 | Steinhauer et al. |
| 2005/0182406 A1 | 8/2005 | Orbay et al. |
| 2006/0189987 A1 | 8/2006 | Orbay et al. |
| 2007/0270849 A1 | 11/2007 | Orbay et al. |
| 2008/0021474 A1 * | 1/2008 | Bonutti ................ A61B 17/844 606/64 |
| 2009/0030466 A1 | 1/2009 | Strauss |
| 2009/0216270 A1 | 8/2009 | Humphrey |
| 2013/0060251 A1 | 3/2013 | Eglseder, Jr. |
| 2014/0031876 A1 | 1/2014 | Spencer |
| 2014/0155944 A1 | 6/2014 | Truman et al. |
| 2014/0163623 A1 | 6/2014 | Humphrey |
| 2015/0094810 A1 | 4/2015 | Leung |
| 2015/0127011 A1 | 5/2015 | Dunlop et al. |
| 2015/0201929 A1 * | 7/2015 | Dooney, Jr. ........ A61B 17/0401 606/225 |
| 2016/0100932 A1 | 4/2016 | Kumar |
| 2016/0166297 A1 | 6/2016 | Mighell et al. |
| 2016/0166298 A1 * | 6/2016 | Mighell ............. A61B 17/0401 606/280 |
| 2017/0042594 A1 | 2/2017 | Conley et al. |
| 2017/0056081 A1 | 3/2017 | Langdale et al. |
| 2017/0100176 A1 | 4/2017 | Kumar |
| 2017/0252080 A1 | 7/2017 | Steinhauer et al. |
| 2018/0028241 A1 | 2/2018 | Levy |
| 2018/0049782 A1 | 2/2018 | Gahman et al. |
| 2018/0049784 A1 | 2/2018 | Gault et al. |
| 2018/0110507 A1 | 4/2018 | Tordi et al. |
| 2018/0193069 A1 | 7/2018 | Levy |
| 2018/0256220 A1 | 9/2018 | Koay et al. |
| 2018/0256221 A1 | 9/2018 | Koay et al. |
| 2018/0256223 A1 | 9/2018 | Lueth et al. |
| 2018/0289402 A1 * | 10/2018 | Lueth ................... A61B 17/866 |
| 2018/0344356 A1 | 12/2018 | Zenker et al. |

OTHER PUBLICATIONS

PCT International Search Report re Application No. PCT/IB2020/056839; dated Oct. 28, 2020; 6 pgs.

* cited by examiner

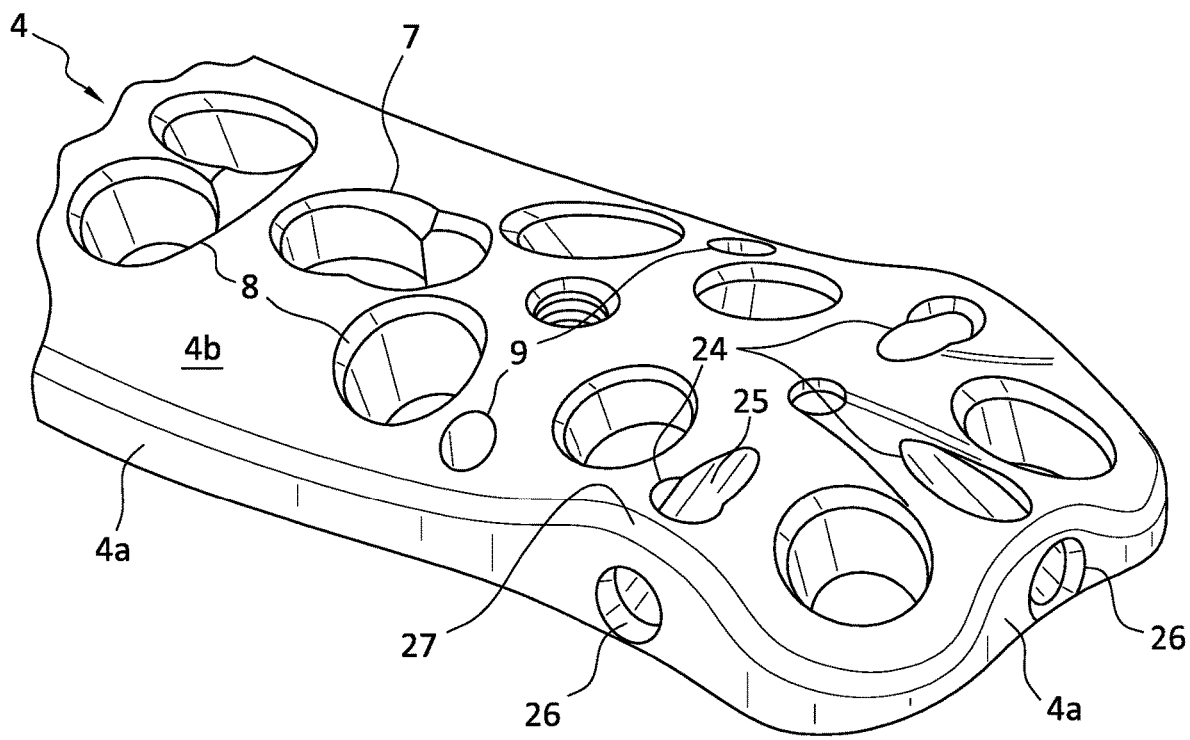
FIG. 7A
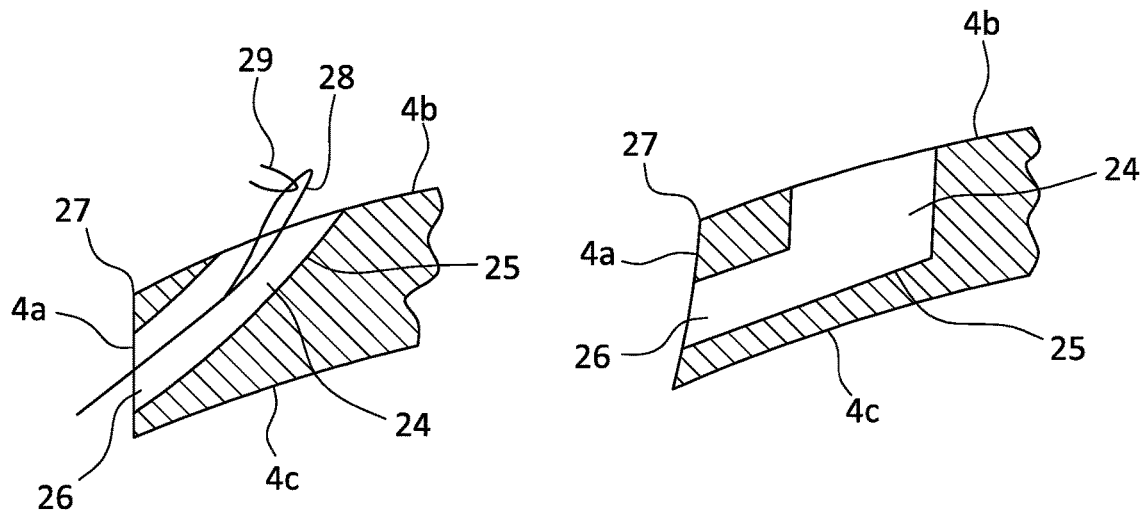
FIG. 7B
FIG. 7C

BONE PLATE WITH STRUCTURES FOR ATTACHMENT OF SUTURES

TECHNICAL FIELD

This disclosure relates generally to bone plates with structures for anchoring sutures to such plates, wherein those sutures had been previously stitched to tendons or ligaments. Various embodiments disclosed herein relate to bone plates configured to be attached to bones, where the plates have structures for anchoring sutures which have been stitched to tendons or ligaments. Various embodiments relate to bone plates configured to be attached to the humerus, where the plates have structures for anchoring sutures stitched to tendons or ligaments in or near the shoulder.

BACKGROUND

Fractured long bones in the arm are often treated using rigid metal or plastic bone plates which may be fixed to the bone or bone fragments using screws or similar fasteners. The screws or other fasteners are attached to the bone on each side of the fracture through apertures in the bone plate. The bone plate may also be provided with suture-receiving holes or structures that allow tendons or ligaments normally connected to the damaged bone to be fixed to the bone plate with sutures, anchoring the tendons or ligaments in place.

SUMMARY

Various embodiments disclosed herein relate to a bone plate system designed to be anchored to a bone, which may be a long bone in the arm or leg, such as a humerus. The system includes an elongated bone plate extending along a longitudinal axis, the bone plate having an upper surface, an opposed bone-facing surface, and a boundary edge. At least one threaded fastener hole extends from the upper surface to the bone-facing surface, the at least one fastener hole being designed to receive a bone fastener, such as a screw, configured to couple the bone plate to the bone. A plurality of first suture-receiving structures connect with the bone plate and project from the boundary edge of the bone plate, so that the suture-receiving structures are spaced from each another along the boundary edge. Each of the plurality of first suture-receiving structures includes a wire loop anchored to the upper surface or the bone-facing surface of the bone plate. In various embodiments, the boundary edge of the bone plate has two opposing side edges and an end edge.

In various embodiments, the bone plate is connected to a humerus, and at least one of the plurality of first suture-receiving structures projects from each opposing side edge of the boundary edge. Each first suture-receiving structure is configured to receive a suture connecting the elongated bone plate to at least one of an infraspinatus tendon, a teres minor tendon, and a subscapularis tendon. In various embodiments, at least one of the plurality of first suture-receiving structures projects from the end edge of the boundary edge, and is configured to receive a suture connecting the elongated bone plate to a supraspinatus tendon.

In various embodiments, at least one of the plurality of first suture-receiving structures projects from each opposing side edge of the boundary edge, and at least one of the plurality of first suture-receiving structures projects from the end edge of the boundary edge. In some embodiments, at least one first suture-receiving structure projects from the end edge of the boundary edge, and is designed to receive a suture connecting the elongated bone plate to a supraspinatus tendon; and at least one first suture-receiving structure projects from each opposing side edge of the boundary edge, and is designed to receive a suture connecting the elongated bone plate to at least one of an infraspinatus tendon, a teres minor tendon, and a subscapularis tendon.

In various embodiments disclosed herein, the first suture-receiving structures projecting from each opposing side edge are formed from a single wire, where the single wire has two ends anchored in wire-receiving holes formed on the opposed bone-facing surface of the bone plate. In embodiments of the bone plate disclosed herein, the opposed bone-facing surface of the bone plate has wire-receiving troughs formed therein; so that at least a portion of the length of the single wire is positioned within the wire-receiving troughs. The troughs on the opposed bone-facing surface of the bone plate are designed to prevent movement of the single wire relative to the opposed bone-facing surface.

In various embodiments, the bone plate includes first suture-receiving structures projecting from the end edge of the bone plate. The first suture-receiving structures projecting from the end edge are formed from a single wire, where the single wire has two ends anchored in wire-receiving holes formed on the opposed bone-facing surface. The opposed bone-facing surface may have wire-receiving troughs having at least a portion of the length of the single wire positioned therein, so that the troughs prevent movement of the single wire relative to the opposed bone-facing surface.

In various embodiments, the bone plate includes first suture-receiving structures projecting from the end edge of the bone plate, where the elongated bone plate has an indented surface on the upper surface of the bone plate near the end edge. The first suture-receiving structures projecting from the end edge are formed from a single wire connected to the indented surface, where the single wire has two ends anchored in wire-receiving holes formed on the indented surface of the bone plate. The bone plate may further include at least one second suture hole structure, wherein the second suture-receiving structure projects from the boundary edge of the bone plate. The at least one second suture-receiving structure is formed from a second single wire, where the second single wire has two ends anchored in wire-receiving holes formed on the opposed bone-facing surface. At least a portion of the length of the second single wire is positioned within the wire-receiving troughs on the opposed bone-facing surface, so that the troughs prevent movement of the single wire relative to the opposed bone-facing surface. At least two second suture-receiving structures may be formed from the second single wire.

In various embodiments, the bone plate includes first suture-receiving structures projecting from the side and/or end edge of the bone plate, and at least one second suture-receiving structure connected with the bone plate. In some embodiments, at least one second suture-receiving structure is a suture-receiving hole extending from the upper surface of the bone plate to one of the opposing side edges or the end edge of the bone plate. Each suture-receiving hole is straight, curved, or angled, and is designed to allow a curved surgical needle to pass therethrough.

In some embodiments, at least one third suture-receiving structure is connected with the bone plate, in addition to the first and/or second suture-receiving structures. The third suture-receiving structure includes a threaded hole; a screw with a threaded shaft; and a washer configured to engage the threaded shaft. The threaded shaft is configured to be wrapped with a suture; and the screw is configured to be screwed into the threaded hole until the suture is compressed between the upper surface of the bone plate and the washer.

In some embodiments, at least one fourth suture-receiving structure is connected with the bone plate, and includes an indented surface in the upper surface of the bone plate, adjacent to the boundary edge of the bone plate. The fourth suture-receiving structure also includes a post mounted on the indented surface, where the post has a first cross-sectional area; and a head mounted on the post, where the head has an upper surface with a second area which is larger than the first cross-sectional area. The post on the fourth suture-receiving structure is configured to allow a suture to be wrapped therearound. The head is designed to prevent a suture wrapped around the post from slipping off the post.

In various embodiments disclosed herein, at least one fifth suture-receiving structure is connected with the bone plate, and includes an indented surface in the boundary edge of the bone plate. The fifth suture-receiving structure also includes a post mounted on the indented surface in the boundary edge, adjacent to the upper surface of the bone plate. The post extends laterally from the indented surface, generally parallel to the upper surface of the bone plate. The post has a first cross-sectional area; and a head mounted on the post, where the head has an upper surface with a second area which is larger than the first cross-sectional area. The post on the fifth suture-receiving structure is configured to allow a suture to be wrapped therearound. The head is designed to prevent a suture wrapped around the post from slipping off the post.

In various embodiments disclosed herein, the bone plate includes:
- first suture-receiving structures projecting from the side and/or end edge of the bone plate, and/or
- at least one second suture-receiving structure connected with the bone plate,
- in combination with at least one third suture-receiving structure.

The first suture-receiving structure includes a wire loop connected to the bone plate and the second suture-receiving structure is a suture-receiving hole extending from the upper surface of the bone plate to an edge of the bone plate. In various embodiments, the bone plate includes a third suture-receiving structure selected from the following:
- a third suture-receiving structure including a threaded hole in the bone plate; a screw with a threaded shaft; and a washer configured to engage the threaded shaft;
- a fourth suture-receiving structure including an indented surface in the upper surface of the bone plate; a post mounted on the indented surface; and a head mounted on the post; and
- a fifth suture-receiving structure including an indented surface in the boundary edge of the bone plate; a post mounted on the indented surface in the boundary edge, extending laterally from the indented surface; and a head mounted on the post.

In light of the present need for improved methods of anchoring damaged tendons and/or ligaments to a bone plate, a brief summary of various exemplary embodiments is presented. The embodiments disclosed herein are illustrative of bone plates with suture-receiving structures, and are not intended to be exhaustive or limiting of the possible devices which can be realized. Some simplifications and omissions may be made in the following summary, which is intended to highlight and introduce some aspects of the embodiments disclosed herein, but not to limit the scope of the disclosed subject matter. Detailed descriptions of various exemplary embodiments adequate to allow those of ordinary skill in the art to make and use the concepts disclosed herein will follow in later sections.

BRIEF DESCRIPTION OF THE DRAWINGS

In order to better understand various exemplary embodiments, reference is made to the accompanying drawings, wherein:

FIGS. 7A to 7C show bone plates with oblique or intersecting suture receiving holes extending from a top of the bone plate to an edge of the bone plate;

DETAILED DESCRIPTION

Figure 1:
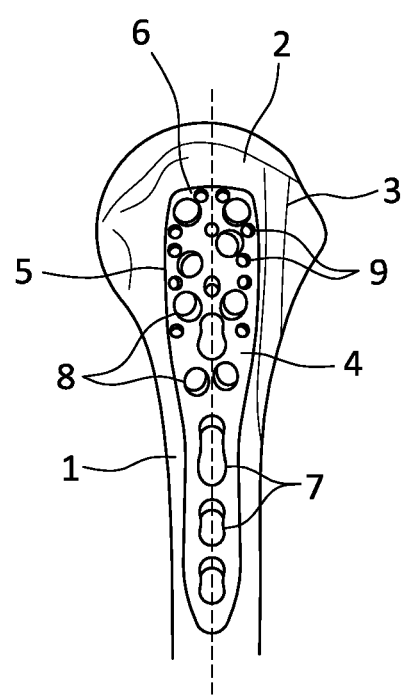
FIG. 1 shows a bone plate positioned for attachment to a humerus bone.

Referring now to the drawings, in which like numerals refer to like components or steps, there are disclosed broad aspects of various exemplary embodiments.

In many bone plates, tendons or ligaments are anchored to the bone plate with sutures, where suture-receiving holes pass from an upper surface of a bone plate to a lower, bone-contacting surface of the bone plate. Since the lower surface of the bone plate contacts the damaged bone, it is difficult to pass a suture through a suture-receiving hole after the bone plate is in position on the bone. Thus, there is a need in the art for bone plates with suture-receiving structures which are not impeded by the bone surface after the bone plate is positioned on a bone.

FIG. 1 shows a bone plate 4 positioned for attachment for attachment to a humerus bone 1, adjacent to the bicep tendon 3. Bone plate 4 has two side edges 5 configured to be positioned along the length of bone 1, and an end edge 6 at a first end of plate 4 positioned over the greater tuberosity 2 of humerus 1. The second end of plate 4 contains a series of holes 7 configured to receive cortical screws driven into the shaft of humerus 1. The first end of plate 4 contains a set of holes 8 configured to receive post screws, where the post screws are configured to affix the bone plate 4 to the head of humerus 1. A series of paired small suture holes 6 are configured to hold sutures anchoring ligaments or tendons to bone plate 4.

One problem with conventional plates of this type is that small suture holes 6 extend from an upper surface of bone plate 4 to a lower, bone-contacting surface of bone plate 4. This makes it difficult to pass a suture through a suture hole 6 after anchoring the bone plate 4 to the bone.

Figure 2:
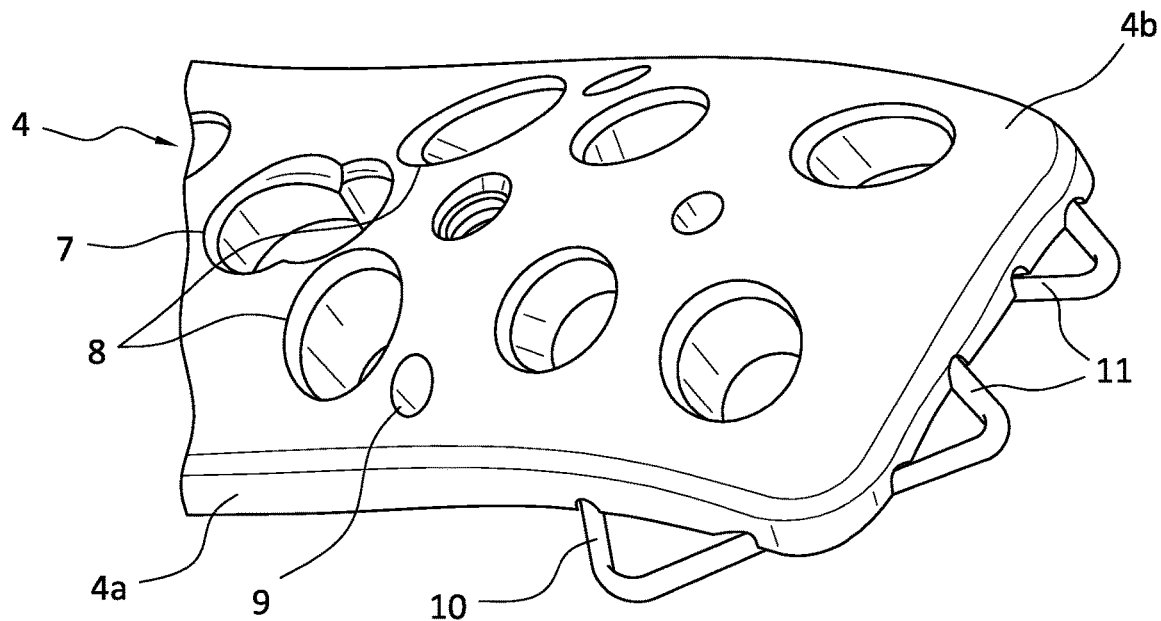
FIG. 2 and FIG. 3 show a bone plate with suture-receiving structures formed from a wire fixed to a bottom of the bone plate forming multiple suture-receiving wire loops.
Figure 3:
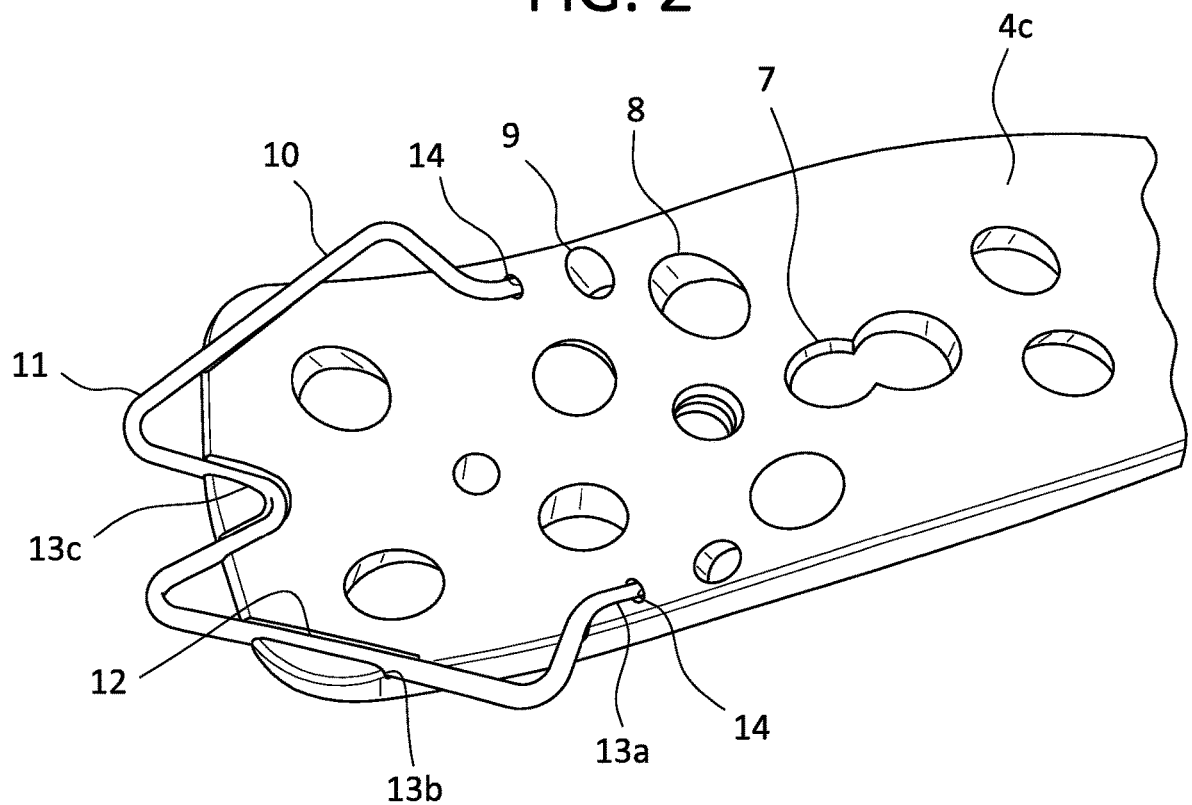

In various embodiments disclosed herein, a bone plate 4 has an upper surface 4b, a lower surface 4c, and a boundary edge surface 4a with opposing side surfaces and an end surface, as shown in FIGS. 2 and 3. At least one first suture-receiving structure 10 formed from a wire loop projects from each opposing side surface of the boundary edge, and is configured to receive a suture connecting the elongated bone plate to at least one of an infraspinatus tendon, a teres minor tendon, and a subscapularis tendon. In various embodiments disclosed herein, at least one first suture-receiving structure 11 formed from a wire loop projects from the end edge of the boundary edge. Suture-receiving structure 11 may be configured to receive a suture connecting the elongated bone plate to a supraspinatus tendon. In addition, holes 9 for k-wire passage may be present on the bone plate 4, along with holes 7 configured to receive cortical screws and holes 8 configured to receive post screws.

As shown in FIG. 3, at least one of the first suture-receiving structures 10 projects from each opposing side edge of the boundary edge 6, and at least one of the first suture-receiving structures 11 projects from the end edge of the boundary edge. In some embodiments, at least one first suture-receiving structure 11 projects from the end edge of the boundary edge, and is designed to receive a suture connecting the elongated bone plate to a supraspinatus tendon; and at least one first suture-receiving structure 10 projects from each opposing side edge of the boundary edge, and is designed to receive a suture connecting the elongated bone plate to at least one of an infraspinatus tendon, a teres minor tendon, and a subscapularis tendon. Suture-receiving structures 10 and 11 are formed from a single wire 12, as shown in FIG. 3. The single wire 12 has two ends anchored in wire-receiving recess 14 formed on the lower, bone-facing, surface 4c of the bone plate. In embodiments of the bone plate disclosed herein, the lower, bone-facing, surface 4c of the bone plate 4 has wire-receiving troughs 13a and, if necessary, troughs 13b and 13c formed therein, as shown in FIG. 3. At least a portion of the length of the single wire 12 is positioned within the wire-receiving troughs. The troughs on the lower, bone-facing, surface 4c of the bone plate 4 are designed to prevent movement of the single wire 12 relative to the bone-facing surface 4c.

As seen in FIG. 3, trough 13a allows the wire to traverse a path from wire-receiving recess 14 to the edge of the lower surface 4c of bone plate 4. The width and depth of trough 13a is equal to the diameter of wire 12, preventing movement of the wire relative to recess 14. If wire loops 10 and 11 are formed on adjacent edges, e.g., a side edge and an end edge of plate 4, a straight trough 13b allows wire 12 to cross from loop 10 to loop 11 directly, with straight trough 13b preventing loops 10 and 11 from shifting relative to the bone-facing surface 4c. If multiple wire loops 10 or 11 are formed on the same edge, e.g., two loops 10 on a side edge or two end loops 11 on an end edge of plate 4, a U-shaped trough 13c allows wire 12 to cross from adjacent loops on a single edge directly, while preventing loops 10 or loops 11 from shifting relative to the bone-facing surface 4c. If desired, wire loops 10 and 11 may be bent upwards, away from the plane of lower surface 4c, by 15° to 50°, 20° to 45°, 20° to 40°, 25° to 35°, or about 30°, so as to make it easier for a surgeon to pass a suture connected to a tendon through a wire loop. If desired, after sutures are connected to wire loops 10 and 11, wire loops 10 and 11 may be bent downwards against the bone surface.

Figure 4A:
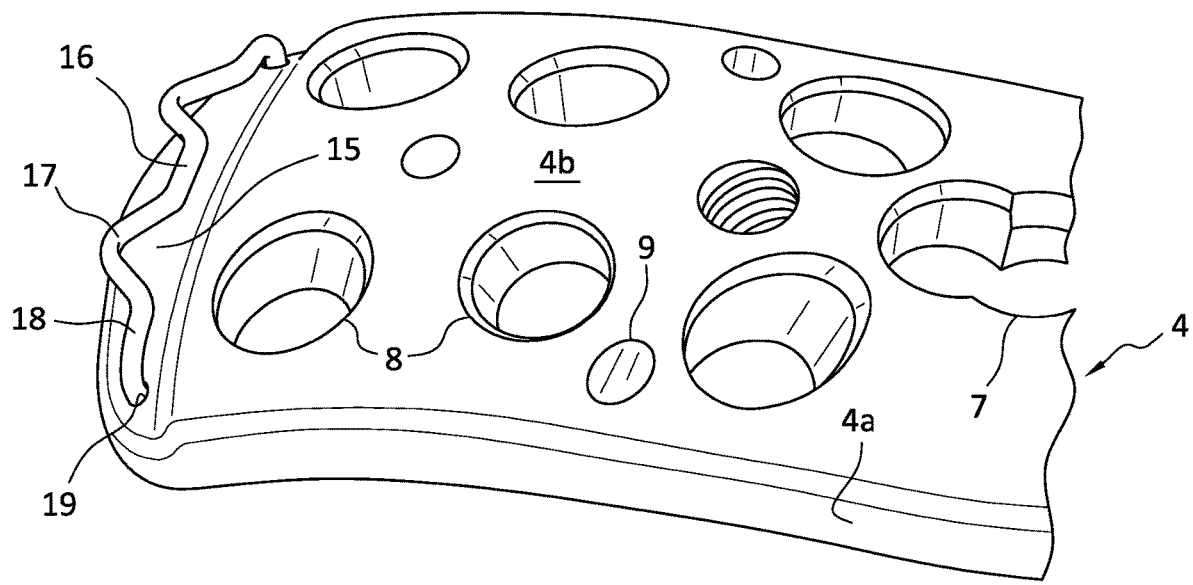
FIGS. 4A and 4B show two embodiments of a bone plate with suture-receiving structures formed from a wire fixed to a top of the bone plate.
Figure 4B:
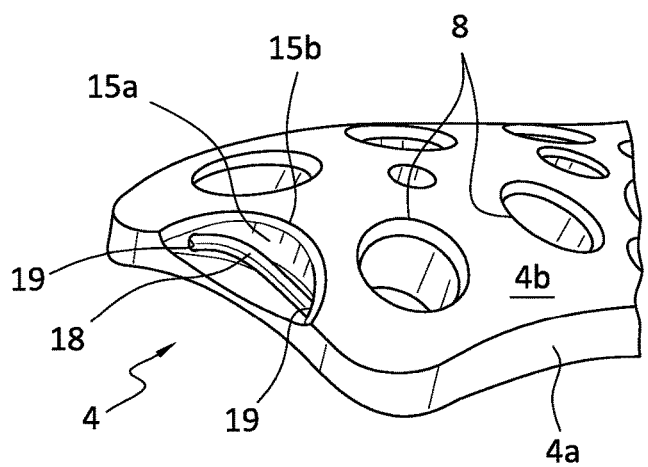

In various embodiments shown in FIGS. 4A and 4B, a bone plate 4 has an upper surface 4b, a lower surface 4c, and a boundary edge surface 4a with opposing side surfaces and an end surface. Bone plate 4 of FIG. 4A may contain holes 9 for k-wire passage, holes 7 configured to receive cortical screws, and holes 8 configured to receive post screws. Near an end of upper surface 4b, a depressed surface or depression 15 is formed in upper surface 4b, with a step between an upper surface of depressed surface 15 and surface 4b. A wire 18 is fastened to depressed surface 15, with the ends of the wire 18 being mounted in wire-receiving holes 19 on surface 15. Wire 18 runs across the bone plate 4 in depression 15, with the wire being bent so as to include at least one v-shaped offset 17 configured to receive a suture connecting the bone plate 4 to a supraspinatus tendon. If wire 18 is bent to include multiple suture-receiving offsets 17, offsets 17 may be separated by a straight length 16 of wire 18. If offsets 17 extend beyond the end of bone plate 4, wire 18 may be positioned so that the length of the wire contacts the upper surface of depression 15. Alternatively, wire 18 may be elevated above the upper surface of depression 15. If loops 17 do not extend beyond the end of bone plate 4, wire 18 may be positioned so that the length of the wire is elevated above the upper surface of depression 15 so as to allow passage of a suture underneath it. In either case, the uppermost portion of wire 18 may be positioned so as to generally be flush with surface 4b of bone plate 4. The upper surface of depression 15 may be below the immediately adjacent portion of surface 4b by a distance which is at least equal to the thickness of wire 18, but less than the thickness of bone plate 4.

In various embodiments shown in FIG. 4B, a bone plate 4 has an upper surface 4b and a boundary edge surface 4a. Bone plate 4 of FIG. 4B may contain holes 7 and 8 configured to receive screws, similar to those seen in FIG. 4A. Near an end of upper surface 4b, a depression 15a with a semicircular or arc-shaped rear wall 15b is formed in upper surface 4b. A wire 18 is fastened in depression 15a, with the ends of the wire 18 being mounted in wire-receiving holes 19. Wire 18 runs across depression 15a, with the wire being bent so as to receive a suture connecting the bone plate 4 to a supraspinatus tendon. Depression 15a may have a depth which is less than the thickness of bone plate 4.

Figure 5:
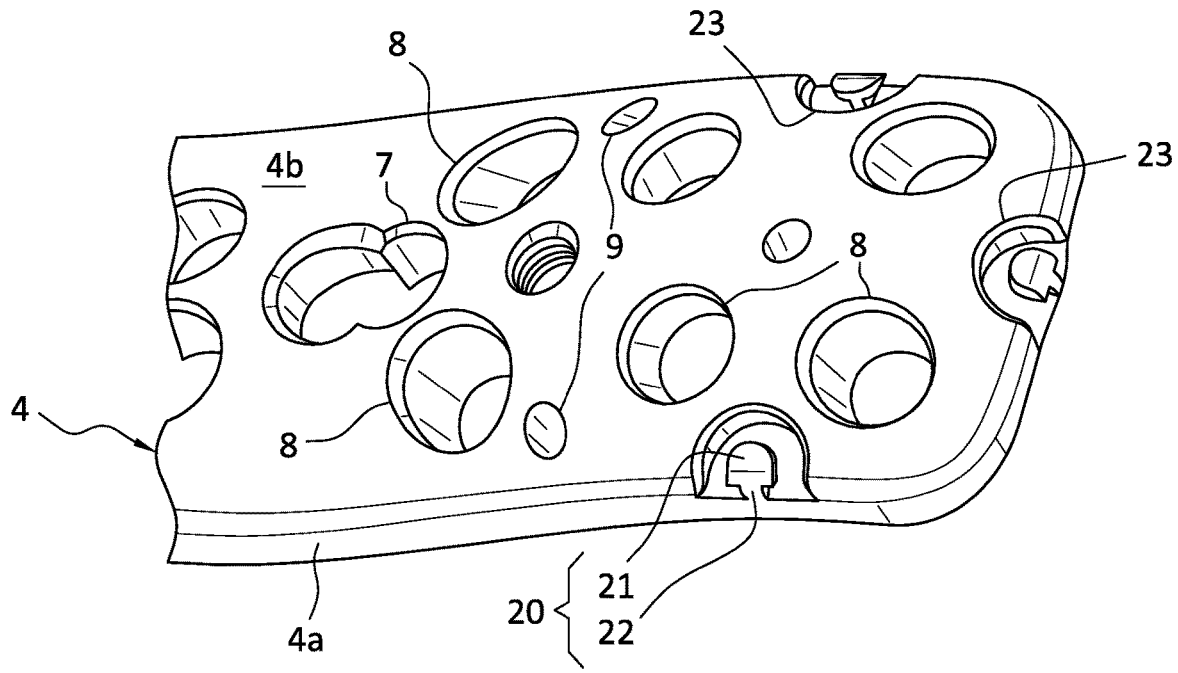
FIGS. 5 and 6 show bone plates with suture receiving cleats formed on an upper surface of a bone plate top of the bone plate.

In various embodiments shown in FIG. 5, a bone plate 4 has an upper surface 4b and a boundary edge surface 4a with opposing side surfaces and an end surface. Bone plate 4 of FIG. 5 may contain holes 9 for k-wire passage, holes 7 configured to receive cortical screws, and holes 8 configured to receive post screws. Depressions 23 are formed in upper surface 4b of bone plate 4, which extend to boundary edge surface 4a of bone plate 4, as seen in FIG. 5. Depressions 23 are formed adjacent to at least one side surface of edge 4a, an end surface of edge 4a, or both side and end surfaces of edge 4a. A cleat 20 is machined in each depression 23. Each cleat 20 includes a post 22 having a first cross sectional area, and a head 21 on post 22, where each head 21 has a second cross sectional area which is greater than the first cross sectional area. Each cleat 20 is configured to receive a suture connecting the bone plate 4 to a tendon or ligament in or near the shoulder. In use, a suture is wrapped around post 22 of suture-receiving cleat 20 and underneath head 21, and tightened to connect the tendon or ligament to the bone plate. Head 21 is larger than post 22, and prevents the suture from sliding off the post and releasing the tendon or ligament when the suture is tensioned.

Figure 6:
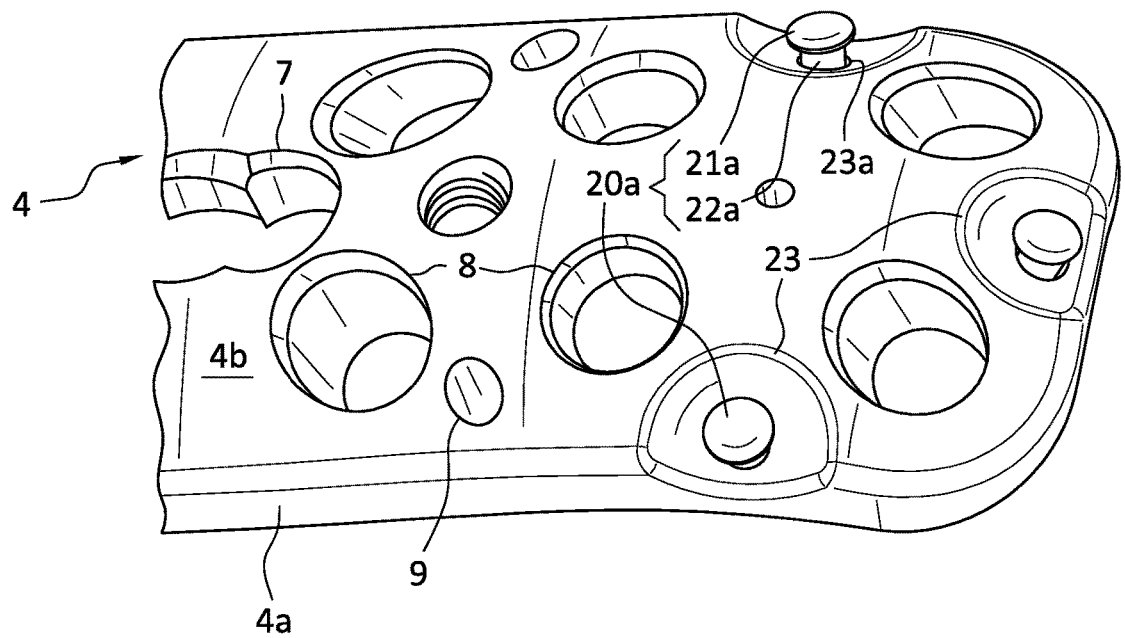

FIG. 6 shows a bone plate 4 with suture-receiving cleats 20a, which are a variant of the cleats 20 in FIG. 5. As seen in FIG. 6, bone plate 4 may contain holes 9 for k-wire passage, holes 7 configured to receive cortical screws, and holes 8 configured to receive post screws. Depressions 23 are formed in upper surface 4b of bone plate 4, which extend to boundary edge surface 4a of bone plate 4, as seen in FIG.

6, and are similar to depressions 23 in FIG. 5. The depressions in FIG. 5 are shown as having a side wall and a planar bottom surface which meet at an angle, which may be a right angle. The depressions in FIG. 6 are shown as being dish- or bowl-shaped. However, dish- or bowl-shaped depressions 23 may be used in the bone plate 4 of FIG. 5, while depressions 23 with planar bottom surfaces may be used in the bone plate 4 of FIG. 6, if desired.

In the bone plate 4 of FIG. 6, a cylindrically symmetric cleat 20a is mounted in each depression 23. Each cleat 20a includes a cylindrical post 22a having a first radius, and a head 21a on post 22a, where each head 21a has a second radius which is greater than the first radius. Each cleat 20a is configured to receive a suture connecting the bone plate 4 to a tendon or ligament. In use, a suture is wrapped around post 22a of suture-receiving cleat 20a and tightened to connect the tendon or ligament to the bone plate. Head 21a prevents the suture from sliding off the post 22a and releasing the tendon or ligament when tensioned. Post 22a of each cleat 20a may fit into a post-receiving hole 23a in the bottom of each depression 23. Post 22a may be secured in hole 23a with an adhesive or by welding or peening. Alternatively, hole 23a be threaded, and a lower portion of post 22a may have a corresponding thread, allowing post 22a to be screwed into hole 23a.

Cleats 20 as shown in FIG. 5 or FIG. 6 may be used in combination with suture-receiving wires 12 of FIG. 3 or 18 of FIG. 4A, if desired. For example, wire 12 may be used to position suture-receiving loops 10 and 11 on the lower surface 4c of bone plate 4, as shown in FIG. 3, while suture-receiving cleats 20 may be mounted in depressions 23 on the upper surface 4b of bone plate 4, as shown in FIG. 5 or FIG. 6. Alternatively, wire 18 may be positioned in depression 15 at the end of upper surface 4b of bone plate 4, as shown in FIG. 4A, while suture-receiving cleats may be mounted in depressions 23, adjacent to a side surface of edge 4a, as shown in FIG. 5.

In various embodiments shown in FIG. 7A, a bone plate 4 has an upper surface 4b and a boundary edge surface 4a, where surface 4a has opposing side surfaces and an end surface. Bone plate 4 of FIG. 7A may contain holes 9 for k-wire passage, holes 7 configured to receive cortical screws, and holes 8 configured to receive post screws. Slanted or oblique suture receiving holes 24 may be used on bone plate 4. As shown in FIG. 7A, suture receiving holes 24 each have an opening on upper surface 4b of bone plate 4 and an opening 26 on boundary edge surface 4a of bone plate 4. Suture receiving holes 24 each have a lower surface 25 along the length of hole 24, and a top 27 at a juncture between surfaces 4a and 4b of bone plate 4.

FIG. 7B shows a partial cross section of the bone plate of FIG. 7A, along an axis of a slanted or oblique suture receiving hole 24. Hole 24 is slanted, and has an axis which forms an angle of about 60° to 80° with boundary edge surface 4a of bone plate 4. Hole 24 has a lower surface 25 and an upper surface 27. A suture needle 28 may be used to draw a suture 29 through hole 24, and the suture may then be looped or tied around top 27 of hole 24.

FIG. 7C shows a partial cross section of an alternate embodiment of the bone plate of FIG. 7A, bisecting a slanted or oblique suture receiving hole 24. Unlike the embodiment of FIG. 7A, hole 24 is nonlinear, and extends downward from surface 4b of bone plate 4 for a portion of the thickness of the bone plate 4, and then extends across to opening 26 in boundary edge 4a of bone plate 4. The portion of hole 24 extending across to opening 26 has a lower surface 25 and an upper surface 27. Hole 24 may be angled, as shown in FIG. 7C, or curved, as desired.

Figure 8:
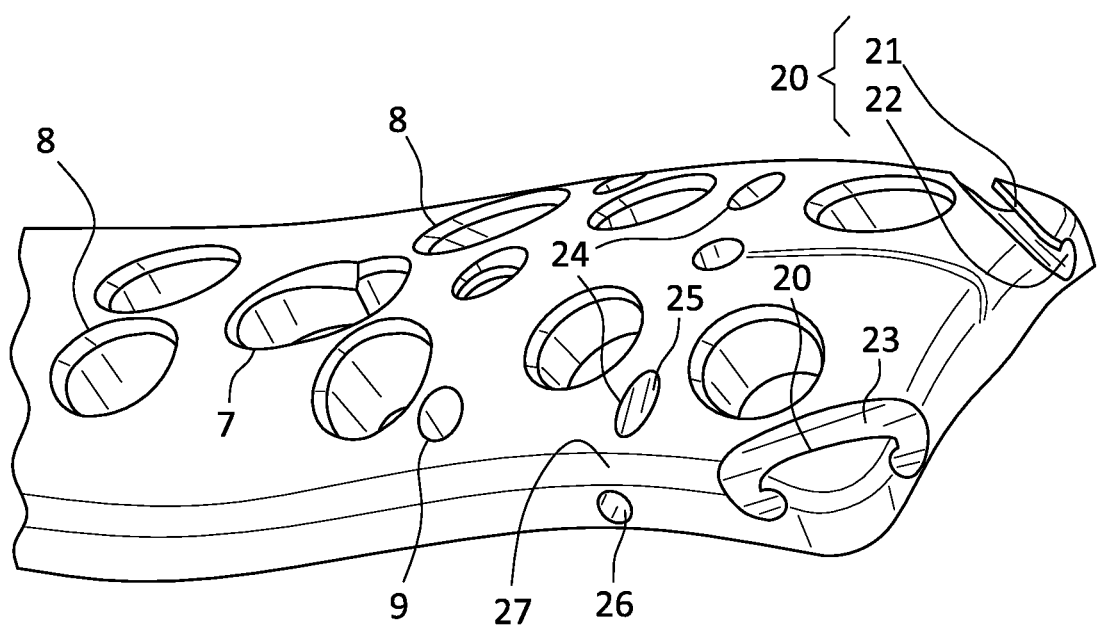
FIG. 8 shows a bone plate with suture receiving cleats formed on the corners of the bone plate.

Oblique suture receiving hole 24 as shown in FIG. 7A to FIG. 7C may be used in combination with suture-receiving wires 12 of FIG. 3 or 18 of FIG. 4A or cleats 20 of FIG. 5, if desired. For example, wire 12 may be used to position suture-receiving loops 10 and 11 on the lower surface 4c of bone plate 4, as shown in FIG. 3, while suture receiving hole 24 may extend from the upper surface 4b of bone plate 4 to the edge surface 4a, as shown in FIG. 7A. Alternatively, suture-receiving cleats may be mounted in depressions 23, adjacent to edge 4a, as shown in FIG. 5, in combination with oblique suture receiving holes 24. FIG. 8 shows oblique suture receiving holes 24, as depicted in FIG. 7A, in combination with suture receiving cleats 20, similar to those of FIG. 5. Cleats 20 of FIG. 8 differ from the cleats 20 of FIG. 5 primarily in that cleats 20 of FIG. 5 ("edge cleats") are positioned on the edge of bone plate 4 in semicircular depressions 23, while cleats 20 of FIG. 8 ("corner cleats") are positioned on the corners of bone plate 4 in triangular depressions 23. Edge cleats 20 and corner cleats 20 may be used separately or in combination, as desired.

As depicted in FIG. 8, corner cleats 20 are formed in triangular depressions 23 in upper surface 4b of bone plate 4, at an intersection between adjacent edges of bone plate 4. A cleat 20 is mounted in each depression 23. Each cleat 20 includes a post 22 having a first cross sectional area, and a head 21 on post 22, where each head 21 has a second cross sectional area which is greater than the first cross sectional area. Each cleat 20 is configured to receive a suture connecting the bone plate 4 to a tendon or ligament in or near the shoulder. In use, a suture is wrapped around post 22 of suture-receiving cleat 20 and tightened to connect the tendon or ligament to the bone plate. Head 21 is larger than post 22, and prevents the suture from sliding off the post and releasing the tendon or ligament.

The edge cleats of FIG. 5 have a head with a semicircular shape, matching the curvature of corresponding depression 23. The corner cleats of FIG. 8 have a head with a linear inner edge, matching the facing edge of corresponding triangular depression 23.

Figure 9:
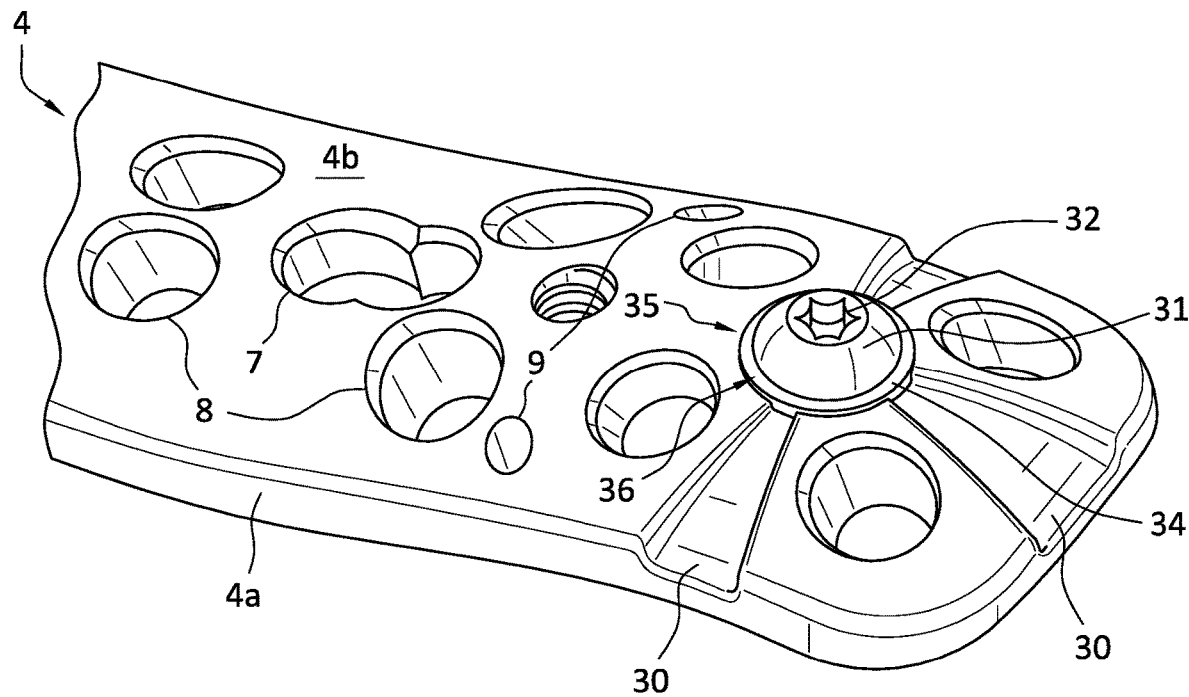
FIGS. 9 and 10 show a bone plate with a central threaded post for anchoring a suture to the bone plate.

In various embodiments shown in FIG. 9, a bone plate 4 has an upper surface 4b and a boundary edge surface 4a, where surface 4a has opposing side surfaces and an end surface. Bone plate 4 of FIG. 9 may contain holes 9 for k-wire passage, holes 7 configured to receive cortical screws, and holes 8 configured to receive post screws. Bone plate 4 of FIG. 9 additionally contains a central suture post 35 configured to anchor a suture to the upper surface 4b of bone plate 4. Central suture post 35 includes a screw 36 with a head 31 and a threaded shaft 33 (not shown in FIG. 9). Screw head 31 has a socket 32 adapted to receive a wrench for driving screw 36. Socket 32 may be configured to receive an orthopedic screwdriver. Wedge-shaped depressions 30 radiate out from central post 35, and are configured to receive sutures extending from central post 35 to a tendon or ligament. The suture wraps around shaft 33 of screw 36, beneath a planar or slightly dish-shaped washer 34. Threaded shaft 33 passes through washer 34 into a threaded hole 37 (not shown in FIG. 9), and screw 36 is screwed into hole 37 until the suture wrapped around the shaft is compressed between the upper surface 4b of bone plate 4 and washer 34. The suture extends to a tendon or ligament, and passes along the surface of bone plate 4 in one of depressions 30, so that the depression walls limit rotation of the suture about the central post.

Figure 10:
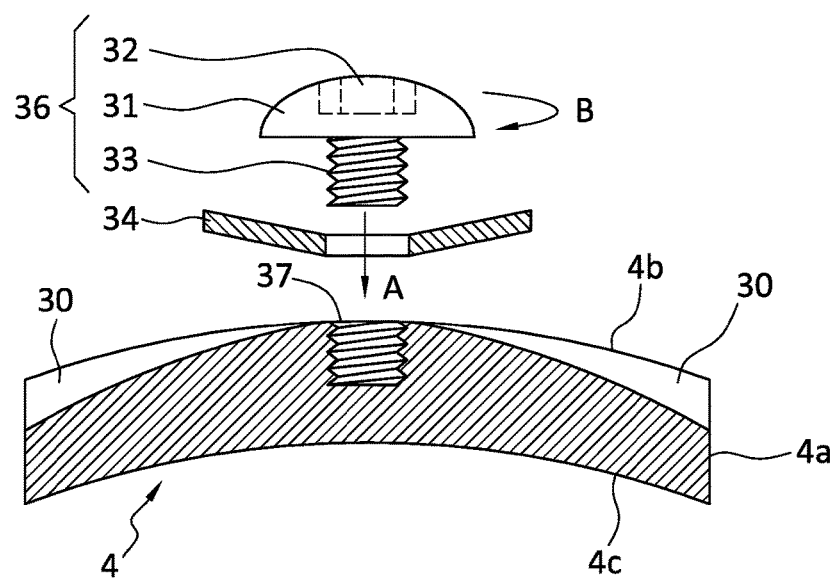

FIG. 10 shows an exploded view of a cross section of bone plate 4 with a central suture post as shown in FIG. 9. Bone plate 4 includes a top surface 4b with wedge-shaped depressions 30 therein, a bottom surface 4c, and a side surface 4a. The narrow end of each wedge-shaped depression 30 is directed toward threaded hole 37, which is configured to receive threaded shaft 33 of screw 36. Shaft 33 of screw 36 passes through washer 34 in the direction of arrow A, and then screws into threaded hole 37, which extends part of the distance from surface 4b to surface 4c, without passing completely through bone plate 4. A suture may be wrapped around screw shaft 33 between washer 34 and upper surface 4b of bone plate 4, and screw 36 may be tightened by rotation in the direction of arrow B until the suture is firmly held between bone plate surface 4b and washer 34.

Figure 11:
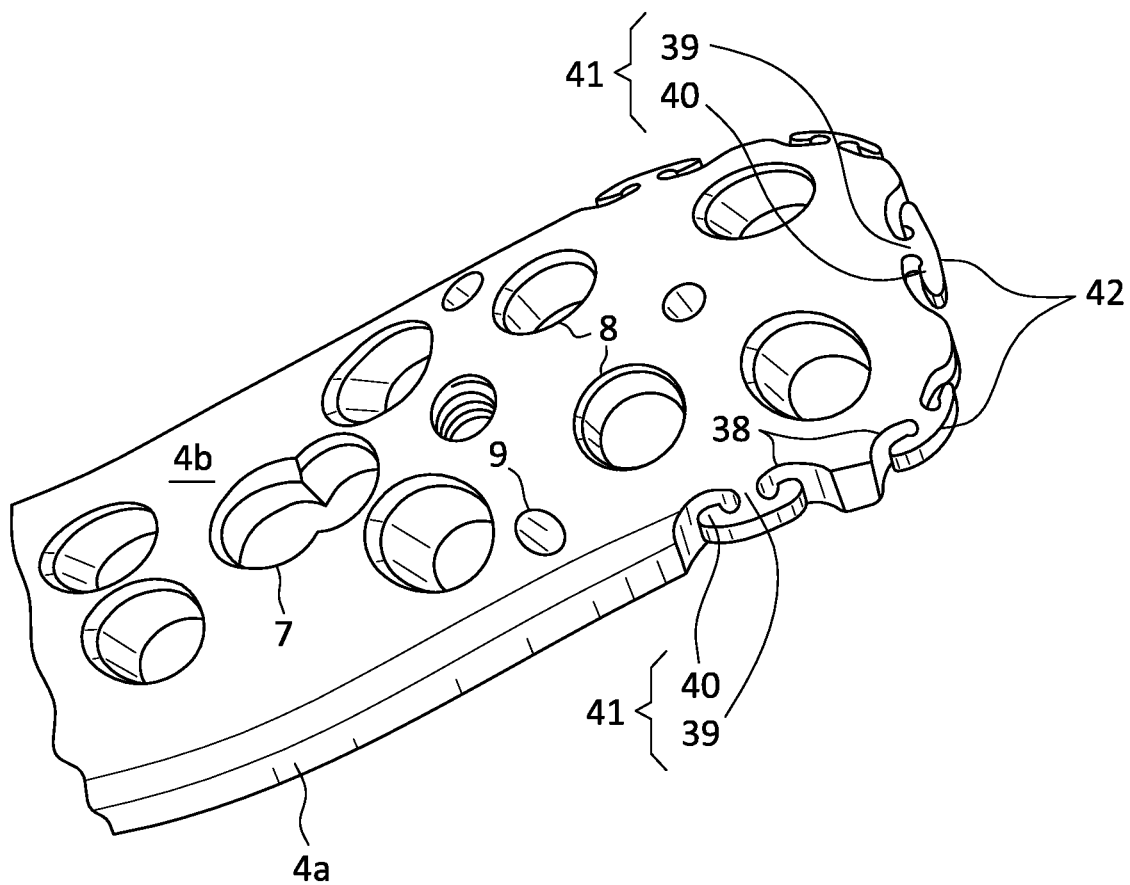
FIG. 11 shows a bone plate with horn-style suture receiving cleats extending from a peripheral edge of the bone plate.

FIG. 11 shows various embodiments of a bone plate 4 with a boundary edge surface 4a with opposing side surfaces and an end surface, with a plurality of T-shaped or horn-style suture-receiving cleats 41. Unlike cleats 20 and 20a of FIGS. 5 and 6, which extend upward from depressions 23 in upper surface 4b of bone plate 4, horn-style cleats 41 extend laterally from edge surface 4a. Cut-out notches 38 are formed in edge 4a of bone plate 4. Each cut-out notch 38 contains a horn-style cleat 41. Each horn-style cleat 41 includes a post 39 extending laterally from the inner edge of notch 38, and a head 40. Each horn-style cleat 41 is configured to receive a suture connecting the bone plate 4 to a tendon or ligament in or near the shoulder. In use, a suture is wrapped around post 39 of horn-style suture-receiving cleat 41 and tightened to connect the tendon or ligament to the bone plate. Head 40 prevents the suture from sliding off of post 39 and releasing the tendon or ligament. Each horn-style cleat 41 includes a generally planar upper surface covering the entire area of post 39 and head 40, where the generally planar upper surface of cleat 41 is flush with upper surface 4b of bone plate 4. Each cleat 41 includes an outer edge surface 42, where the outer edge surface 42 is flush with boundary edge surface 4a of bone plate 4. Each cleat 41 has a thickness which is less than the thickness of bone plate 4 at edge surface 4a, e.g., from 25% to 70%, from 30% to 70%, from 35% to 65%, from 40% to 60%, or from 45% to 55% of the thickness of boundary edge 4a.

Although the various exemplary embodiments have been described in detail with particular reference to certain exemplary aspects thereof, it should be understood that the present disclosure affords embodiments, and its details are capable of modifications in various obvious respects. As is readily apparent to those skilled in the art, variations and modifications can be affected while remaining within the spirit and scope of the subject matter disclosed herein. Accordingly, the foregoing disclosure, description, and figures are for illustrative purposes only and do not in any way limit the invention, which is defined only by the claims.

What is claimed is:

1. A bone plate system for use on a bone, the system comprising:
    an elongated bone plate extending along a longitudinal axis, the bone plate having an upper surface, an opposed bone-facing surface, and a boundary edge surface of the bone plate, wherein the boundary edge surface connects the upper surface to the opposed bone-facing surface;
    at least one fastener hole extending from the upper surface to the bone-facing surface, the at least one fastener hole being configured to receive a bone fastener configured to couple the bone plate to the bone;
    a plurality of first suture-receiving structures connected with the bone plate and projecting from the boundary edge surface of the bone plate, the first suture-receiving structures being spaced from each another along the boundary edge surface; and
    a second suture-receiving structure comprising a suture-receiving hole with a lower surface, the lower surface of the suture-receiving hole extending from the upper surface of the bone plate to the boundary edge surface of the bone plate without intersecting the bone-facing surface of the bone plate;
        wherein each of the plurality of first suture-receiving structures comprises a wire loop, wherein each wire loop is anchored to the upper surface or the bone-facing surface of the bone plate without engaging the suture receiving hole of the second suture-receiving structure.

2. The bone plate system of claim 1, wherein:
the bone is a humerus;
the boundary edge surface of the bone plate has two opposing side edges and an end edge; and
at least one of the plurality of first suture-receiving structures projects from each opposing side edge of the boundary edge surface, and is configured to receive a suture connecting the elongated bone plate to at least one of an infraspinatus tendon, a teres minor tendon, or a subscapularis tendon.

3. The bone plate system of claim 1, wherein:
the first suture-receiving structures are formed from a single wire; and
the single wire has two ends anchored in wire-receiving holes formed into the plate surface, which may or may not extend to the opposed bone-facing surface.

4. The bone plate system of claim 3, wherein:
the opposed bone-facing surface has wire-receiving troughs formed therein;
at least a portion of the length of the single wire is positioned within the wire-receiving troughs; and
the troughs are configured to prevent movement of the single wire relative to the opposed bone-facing surface.

5. The bone plate system of claim 1, wherein:
the bone is a humerus;
the boundary edge surface of the bone plate has two opposing side edges and an end edge; and
at least one of the plurality of first suture-receiving structures projects from the end edge of the boundary edge surface, and is configured to receive a suture connecting the elongated bone plate to a supraspinatus tendon.

6. The bone plate system of claim 5, wherein:
the first suture-receiving structures are formed from a single wire; and
the single wire has two ends anchored in wire-receiving holes formed on the opposed bone-facing surface.

7. The bone plate system of claim 6, wherein:
the opposed bone-facing surface has wire-receiving troughs formed therein;
at least a portion of the length of the single wire is positioned within the wire-receiving troughs; and
the troughs are configured to prevent movement of the single wire relative to the opposed bone-facing surface.

8. The bone plate system of claim 5, wherein:
the elongated bone plate has an indented surface on the upper surface of the bone plate near the end edge;
the first suture-receiving structures projecting from the end edge are formed from a single wire connected to the indented surface; and the single wire has two ends anchored in wire-receiving holes formed on the indented surface of the bone plate.

9. The bone plate system of claim 8, further comprising:
at least one third suture-receiving structure, wherein the at least one third suture-receiving structure projects from the boundary edge surface of the bone plate,
wherein the at least one third suture-receiving structure is formed from a second single wire; and
the second single wire has two ends anchored in wire-receiving holes formed on the opposed bone-facing surface.

10. The bone plate system of claim 9, wherein:
the opposed bone-facing surface has wire-receiving troughs formed therein;
at least a portion of the length of the second single wire is positioned within the wire-receiving troughs; and
the troughs are configured to prevent movement of the second single wire relative to the opposed bone-facing surface.

11. The bone plate system of claim 1, wherein:
the boundary edge surface of the bone plate has two opposing side edges and an end edge at least one of the plurality of first suture-receiving structures projects from each opposing side edge of the boundary edge surface, and
at least one of the plurality of first suture-receiving structures projects from the end edge of the boundary edge surface.

12. The bone plate system of claim 11, wherein:
wherein the first suture-receiving structures projecting from the side edge and the first suture-receiving structures projecting from the end edge are formed from a single wire;
wherein the single wire has two ends anchored in wire-receiving holes formed on the opposed bone-facing surface.

13. The bone plate system of claim 12, wherein:
the opposed bone-facing surface has wire-receiving troughs formed therein;
at least a portion of the length of the single wire is positioned within the wire-receiving troughs; and
the troughs are configured to prevent movement of the second single wire relative to the opposed bone-facing surface.

14. The bone plate system of claim 1, further comprising:
at least one third suture-receiving structure connected with the bone plate;
wherein each third suture-receiving structure comprises a threaded hole; a screw with a threaded shaft, and a washer configured to engage the threaded shaft;
wherein the threaded shaft is configured to be wrapped with a suture; and
wherein the screw is configured to be screwed into the threaded hole until the suture is compressed between the upper surface of the bone plate and the washer.

15. The bone plate system of claim 1, further comprising:
at least one third suture-receiving structure connected with the bone plate;
wherein each third suture-receiving structure comprises an indented surface in the upper surface of the bone plate and a cleat mounted on the indented surface;
each cleat comprising a post mounted on the indented surface, the post having a first cross-sectional area; and
a head mounted on the post, the head having an upper surface with a second area which is larger than the first cross-sectional area.

16. The bone plate system of claim 1, wherein each wire loop is anchored to the bone-facing surface of the bone plate.

17. A bone plate system for use on a bone, the system comprising:
an elongated bone plate extending along a longitudinal axis, the bone plate having an upper surface, an opposed bone-facing surface, and a boundary edge surface of the bone plate, wherein the boundary edge surface connects the upper surface to the opposed bone-facing surface;
at least one fastener hole extending from the upper surface to the bone-facing surface, the at least one fastener hole being configured to receive a bone fastener configured to couple the bone plate to the bone; and
at least one first suture-receiving structure in the bone plate;
wherein each first suture-receiving structure comprises a suture-receiving hole with a lower surface, the lower surface of the suture-receiving hole extending from the upper surface of the bone plate to the boundary edge surface of the bone plate without intersecting the bone-facing surface of the bone plate;
wherein each suture-receiving hole is straight, curved, or angled;
wherein each suture-receiving hole is configured to receive a suture therethrough; and
wherein the bone plate system further comprises:
at least one second suture-receiving structure connected with the bone plate;
wherein each second suture-receiving structure comprises a threaded hole in the upper surface of the bone plate; a screw with a threaded shaft, and a washer configured to engage the threaded shaft;
wherein the threaded shaft is configured to be wrapped with a suture;
wherein the screw is configured to be screwed into the threaded hole until the suture is compressed between the upper surface of the bone plate and the washer; and
wherein the threaded hole in the upper surface of the bone plate does not extend to the bone-facing surface of the bone plate.

18. The bone plate system of claim 17, further comprising:
at least one third suture-receiving structure connected with the bone plate;
wherein each third suture-receiving structure comprises a depression in the upper surface of the bone plate and a cleat in the depression,
each cleat including a post having a first cross-sectional area, and a head connected to the post, where each head has a second cross sectional area which is greater than the first cross sectional area;
each cleat being configured to receive a suture connecting the bone plate to a tendon or ligament by wrapping the suture around the post.

19. The bone plate system of claim 17, wherein the lower surface of the first suture-receiving hole is between the upper surface of the bone plate and the opposed bone-facing surface of the bone plate.

20. A bone plate system for use on a bone, the system comprising:
an elongated bone plate extending along a longitudinal axis, the bone plate having an upper surface, an opposed bone-facing surface, and a boundary edge surface of the bone plate, wherein the boundary edge surface connects the upper surface to the opposed bone-facing surface;

at least one fastener hole extending from the upper surface to the bone-facing surface, the at least one fastener hole being configured to receive a bone fastener configured to couple the bone plate to the bone;

a suture-receiving hole configured to receive a suture therethrough, said suture-receiving hole extending from the upper surface to the boundary edge surface, wherein the suture-receiving hole has a lower surface between the upper surface of the bone plate and the opposed bone-facing surface of the bone plate; and a second suture-receiving structure comprising a threaded hole extending partially through the bone plate; a screw with a threaded shaft, and a washer configured to engage the threaded shaft;

wherein the threaded shaft is configured to be wrapped with a suture; and wherein the screw is configured to be screwed into the threaded hole until the suture is compressed between the upper surface of the bone plate and the washer.

* * * * *